(12) United States Patent
Xu

(10) Patent No.: US 11,732,275 B2
(45) Date of Patent: Aug. 22, 2023

(54) CELL MICROINJECTION SYSTEM WITH FORCE FEEDBACK

(71) Applicant: UNIVERSITY OF MACAU, Macau (CN)

(72) Inventor: Qingsong Xu, Macau (CN)

(73) Assignee: UNIVERSITY OF MACAU, Macau (CN)

( * ) Notice: Subject to any disclaimer, the term of this patent is extended or adjusted under 35 U.S.C. 154(b) by 1148 days.

(21) Appl. No.: 16/364,458

(22) Filed: Mar. 26, 2019

(65) Prior Publication Data

US 2019/0292567 A1    Sep. 26, 2019

Related U.S. Application Data

(60) Provisional application No. 62/647,947, filed on Mar. 26, 2018.

(51) Int. Cl.
*C12N 15/89* (2006.01)
*B01L 3/00* (2006.01)
(Continued)

(52) U.S. Cl.
CPC ............. *C12N 15/89* (2013.01); *A61D 19/00* (2013.01); *B01L 3/56* (2013.01); *B25J 7/00* (2013.01);
(Continued)

(58) Field of Classification Search
CPC ...... C12N 15/89; C12N 15/0604; H02N 2/02; H02N 2/021; H02N 2/06; B25J 9/1633; B25J 9/1694; B25J 9/1697; B25J 7/00; B25J 19/021; B01L 3/56; B01L 2300/0663; B01L 2300/0672; Y10S 700/00; Y10S 700/90; G05B 13/021; G05B 13/024;
(Continued)

(56) References Cited

U.S. PATENT DOCUMENTS 4,768,521 A * 9/1988 Schiffman ............ A61B 5/4824
600/587
5,350,671 A * 9/1994 Houghton ............ C07K 16/109
435/5
(Continued)

*Primary Examiner* — Emily P Pham
(74) *Attorney, Agent, or Firm* — Nath, Goldberg & Meyer; Joshua B. Goldberg

(57) ABSTRACT

A novel piezo-driven cell injection system with force feedback overcomes the unsatisfied force interaction between the pipette needle and embryos in conventional position control. By integrating semiconductor strain-gage sensors for detecting the cell penetration force and the micropipette relative position in real time, the developed cell microinjection system features high operation speed, confident success rate, and high survival rate. The effectiveness of the developed cell injection system is experimentally verified by penetrating zebrafish embryos. The injection of 100 embryos are conducted with separate position control and force control. Results indicate that the force control enables a survival rate of 86%, which is higher than the survival rate of 82% produced by the position control in the same control environment. The experimental results quantitatively demonstrate the superiority of force control over conventional position control for the first time.

17 Claims, 12 Drawing Sheets
(11 of 12 Drawing Sheet(s) Filed in Color)

(51) Int. Cl.
*A61D 19/00* (2006.01)
*C12N 5/073* (2010.01)
*B25J 9/16* (2006.01)
*B25J 19/02* (2006.01)
*G05B 13/02* (2006.01)
*G05B 19/02* (2006.01)
*H02N 2/02* (2006.01)
*H02N 2/06* (2006.01)
*B25J 7/00* (2006.01)

(52) U.S. Cl.
CPC ........... *B25J 9/1633* (2013.01); *B25J 9/1694* (2013.01); *B25J 9/1697* (2013.01); *B25J 19/021* (2013.01); *C12N 5/0604* (2013.01); *G05B 13/021* (2013.01); *G05B 13/024* (2013.01); *G05B 19/02* (2013.01); *H02N 2/02* (2013.01); *H02N 2/021* (2013.01); *H02N 2/06* (2013.01); *B01L 2300/0663* (2013.01); *B01L 2300/0672* (2013.01); *G05B 2219/2208* (2013.01); *G05B 2219/2214* (2013.01); *G05B 2219/42073* (2013.01); *G05B 2219/42074* (2013.01); *Y10S 700/00* (2013.01); *Y10S 700/90* (2013.01)

(58) Field of Classification Search
CPC .... G05B 2219/2208; G05B 2219/2214; G05B 2219/42073; G05B 2219/42074; G05B 19/02; A61D 19/00
See application file for complete search history.

(56) References Cited

U.S. PATENT DOCUMENTS

| | | | |
|---|---|---|---|
| 6,507,391 B2 * | 1/2003 | Riley | G01N 15/147 356/28 |
| 2006/0051735 A1 * | 3/2006 | Fuhr | C12M 33/02 435/287.1 |
| 2007/0294780 A1 * | 12/2007 | Kawamura | C12N 5/0609 435/325 |
| 2009/0093775 A1 * | 4/2009 | Raju | A61M 37/0015 604/272 |
| 2011/0027885 A1 * | 2/2011 | Sun | C12N 15/89 435/375 |
| 2012/0270256 A1 * | 10/2012 | Oldham | A61B 1/2733 362/319 |
| 2013/0154292 A1 * | 6/2013 | Savran | B25J 15/12 294/196 |
| 2018/0002170 A1 * | 1/2018 | Seger | G01Q 60/44 |

* cited by examiner

CELL MICROINJECTION SYSTEM WITH FORCE FEEDBACK

CROSS REFERENCE TO RELATED APPLICATION

This application claims priority from provisional application 62/647,947 filed on Mar. 26, 2018.

FIELD OF THE INVENTION

The present invention relates to a piezo-driven microinjection system with force feedback suitable for use in biological cell micromanipulation. The invention may also find use in injection of material into other pierceable microstructure targets, such as viruses when used with injectors of appropriate dimensions.

BACKGROUND OF THE INVENTION

Biological cell micromanipulation involves the operation of gripping, injection, cutting, etc. for biological cells. Cell injection is the process of delivering exogenous materials into cells, which is a common operation in biological experiments. Cell injection has been widely applied in genetic engineering, intracytoplasmic sperm injection (ICSI), DNA therapy or other biomedical areas. Comparison study of the human reference genome shows that approximately 70% of human genes have at least one obvious zebrafish orthologue [1], which leads to the widespread use of zebrafish embryo in disease study and drug testing. With advantages of flexibility and efficiency, micropipette injection method has been extensively used in traditional manual cell manipulations. However, the cell injection process requires precision control of the pipette to execute accurate puncturing, injecting, and retracting tasks. It usually requires a long training time for human operators while results in low success rate. The reason lies in that human operators suffer from fatigue problems when injecting a large batch of cells. To overcome such weakness, automated injection technologies have been widely investigated over the last few decades. For example, a microrobotic system with a hybrid visual servo control for automatic cell injection has been developed in [2], which greatly reduces the manipulation time and improves the injection success rate. Optical tweezers have been introduced to conduct cell patterning for the execution of the required operation [3]. A comprehensive review of recent automated microinjection systems has been presented in [4].

There are two main criteria in cell injection, i.e. success rate and survival rate. Image-based visual servo is the dominant control method in existing automatic cell injection systems [5-7]. However, the pipette location, which is extracted by an image processing algorithm, is not absolutely synchronous with the cell status due to the time delay induced by the image acquisition and processing procedure. The vision-based feedback is difficult to identify whether the pipette has pierced in or slipped off the cell during the operation. As a result, a low success rate of cell injection is caused. Meanwhile, it has been reported that a higher success rate will be achieved with force feedback intervened [8]. In the literature, the cell force model has been developed by bulk-scale methods, which rely on the average value of hundreds or thousands of cells. But the individual cell's characteristics would be obscure among the cell group [9]. For an accurate measurement of the exerted force, a microinjection prototype with the integration of a piezoresistive micro-force sensor was developed for zebrafish embryos [10]. It can synchronize the position control with force profile during the injection process. In addition, PVDF (Polyvinylidene Fluoride) films have been used for force sensing during cell injection [11,12].

To improve the cell survival rate, it is necessary to minimize the adverse effect of deformation for the zebrafish embryos induced by the injection force. To cope with this problem, piezoelectric actuators (PZTs) with the advantages of the fast response, high acceleration and precision positioning resolution can be adopted [13]. Piezo-driven micropipettes were first introduced into cell injection by Kimura [14], in which the pipette was driven by a serial of piezo-pules to execute mouse oocytes injection. A survival rate of 80% was achieved in that experiment, while only 16% of the oocytes survived with conventional method. Afterwards, several remarkable research works have been conducted with piezo-driven cell injection system [15-20]. However, all of these works are conducted based on the vibration character of PZTs. It means that the PZT acts like a vibration drill and it is combined with the other actuators to perform the cell injection tasks. Thus, the PZTs' high resolution of displacement is not effectively exploited in these cases.

Commercially available piezoelectric actuators (PZTs) can only provide a limited output displacement (32 μm in this work). It is not large enough to pierce zebrafish embryos with diameter of 600-1200 μm. Hence, a displacement amplifier is required to meet the motion range requirement. Moreover, the injector pipette should experience a pure in-plane translation by avoiding lateral movement, because the latter can induce extra damage to the penetrated cells.

In the literature, piezo displacement amplifiers have been researched extensively [21] and are mainly used for micro/nano manufacturing, atomic force microscopy (AFM), and so on. In this work, a piezo-driven flexure-based injector is designed with a bridge-type displacement amplifier, as shown in FIG. 1.

Referring to FIG. 1, the output direction of PZT is orthogonal to the injection direction. The two leaf flexures in the outside frame are used to guide the linear motion so as to achieve a high positioning precision of in-plane motion. As compared with a parallelogram-based amplifier system, the introduced displacement amplifier reduces the number of guiding flexures and simplifies the structure design, which indicates a reduction of space requirement and fabrication cost.

Assuming that each flexure binge offers a one-degree-of-freedom (1-DOF) rotational compliance which arises from the bending deformation, and other elements are rigid bodies, the displacement output in the injection direction can be calculated by [22]:

$$\Delta y = l_p \sin \alpha - \sqrt{l_p^2 \sin^2 \alpha - \Delta x^2 - 2l_p \cos \alpha \Delta x} \tag{1}$$

Then, the amplification ratio of the bridge-based amplifier can be derived as:

$$R = \frac{\Delta y}{\Delta x} = \frac{l_p \sin \alpha - \sqrt{l_p^2 \sin^2 \alpha - \Delta x^2 - 2l_p \cos \alpha \Delta x}}{\Delta x} \tag{2}$$

TABLE 1

Main parameters of the compliant injector.

| Symbol | Parameter | Value |
| --- | --- | --- |
| $L_1$ | Length of amplifier arm | 9.0 mm |
| $L_2$ | Length of amplifier flexure | 4.5 mm |
| H | Width of amplifier arm | 1.0 mm |
| T | Width of amplifier flexure | 0.5 mm |

As a case design, the main parameters of the injector mechanism are selected as shown in Table 1. With a driving displacement of 32 μm, analytical modelling predicts an output displacement of 350 μm. Finite-element analysis (FEA) is conducted with ANSYS software, the configuration and simulation result can be found in FIG. 2. They indicate an output displacement of 398 μm, and the analytical model result is 13.7% smaller than the FEA simulation result. The discrepancy is mainly caused by the assumption introduced in the analytical model, which only considers the compliance of flexure hinges.

SUMMARY OF THE INVENTION

To make full use of the ultrahigh displacement resolution of PZT, the PZT is adopted as linear actuator with a flexure guiding mechanism to drive the pipette directly for executing cell injection in this work. However, up to now, it is unknown to what extent that the force control performs better than the position control in biological cell injection manipulation. In this work, a piezoelectric actuator with a displacement amplifier is designed to drive the injection pipette. Both position and force sensors are integrated into the device to achieve a higher compactness. Comparative studies with position control and force control have been carried out by experimental injection of 100 zebrafish embryos, and some remarkable conclusions are derived. To the knowledge of the author, no such work has been conducted before in the literature.

Accordingly, from a first aspect, the present invention provides a device, for example for use with a micro injection pipette, said device comprising a linear actuator with position and force strain gauge sensors. Such actuator may be a piezoelectric actuator with a displacement amplifier and the strain gauge sensors may be semiconductor strain gauge sensors.

From a second aspect, the invention provides a microinjection system combining such device and a microinjection pipette. Typically such a system includes a flexure guiding mechanism for driving the pipette to its intended location and for ensuring withdrawal of the pipette with minimal damage to the target. Microinjection pipettes for use in the invention will be chosen with appropriate dimensions based on the nature of the pierceable microstructure target such that when the target is, for example a virus, a pipette with a smaller tip may be used than in the case where the target is a cell or embryo.

The microinjection system of the present invention features low cost, convenient installation, and easy maintenance. A flexure-based displacement amplifier is designed to enlarge the stroke of PZT. With the integration of strain gage sensors, the position and force status of the injected embryos is monitored in real time. This system enables a high operation speed, confident success rate, and high survival rate.

From a third aspect the invention provides a method for microinjection of a substance into a pierceable microstructure such as a biological cells, nuclear envelopes and viral capsids and envelopes using such a piezoelectric actuator.

Such methods may be used in genetic engineering to introduce DNA into a nucleus or virus, including gene therapy, for example in treatment of cancer, in vitro fertilization of an ova, cloning techniques and insertion of cells, such as stem cells, into an embryo.

BRIEF DESCRIPTION OF THE DRAWINGS

The patent application file contains at least one drawing executed in color. Copies of this patent or application publication with color drawings will be provided by the office on request and payment of the necessary fee.

DETAILED DESCRIPTION OF THE INVENTION

Microinjection has two main requirements namely that the injection needle is aligned with the target and that the needle remains within the target while the desired material is being injected into the target.

The present invention provides a new injector system with both position and force sensors. Such system typically further includes a micromanipulator and optical microscope to assist in aligning the injector with the target.

Suitable piezoelectric actuators for use in the present invention include piezoelectric stacks in rectangular, parallelepiped or cylindrical shapes.

Suitable displacement amplifiers include bridge-type and compound bridge type flexure-based amplifiers.

Suitable integrated position sensors include resistance based and capacitive-based sensors.

Suitable force sensors include resistance-based and capacitive-based sensors. Suitable injection pipettes include glass micropipettes and metal micropipettes.

Figure 1:
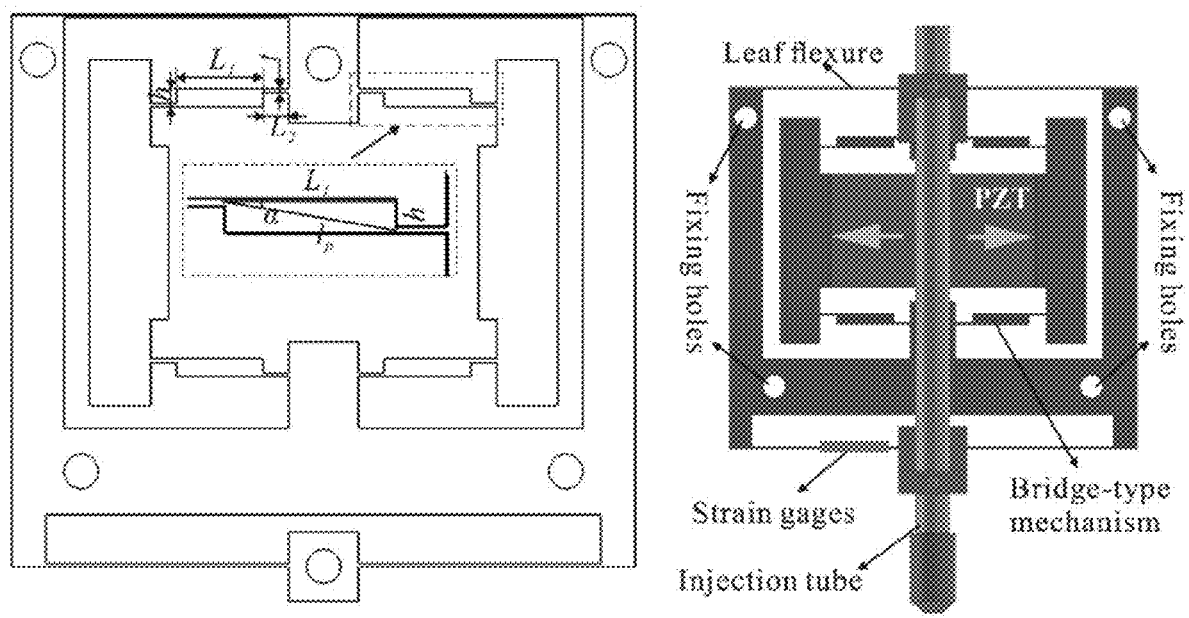
FIG. 1 is a schematic diagram of the flexure-based injector, which is driven by a PZT with a bridge-type displacement amplifier.
Figure 2:
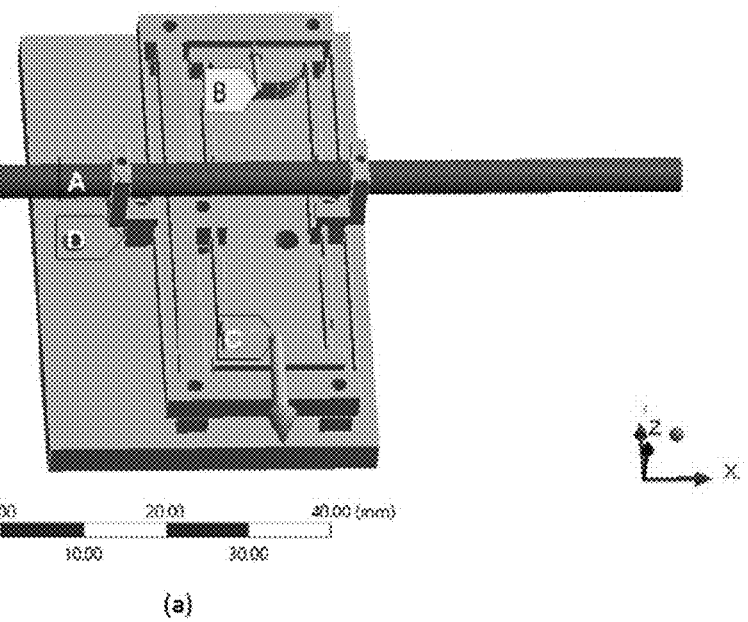
FIG. 2 shows FEA simulation results of the injector. (a) FEA analysis configuration. (b) FEA analysis result.
Figure 2:
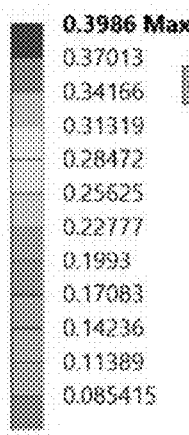

The components of the system are configured so that the piezoelectric actuator provides an accurate location of the target for injection such as a biological cell, for example by use of a bridge-type displacement amplifier of the type shown in FIG. 1. Furthermore the sensors are configured to enable control of the force used to puncture the target and effect retraction from the target after injection has been completed. Information from the sensors is used to control the movement of the pipette, for example by use of a proportional-integral-derivative (pid) controller.

Figure 8:
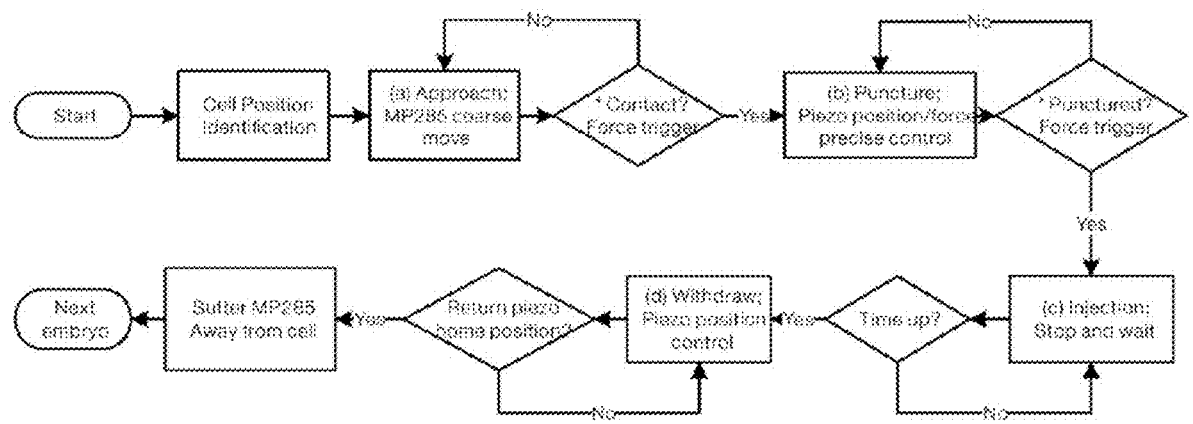
FIG. 8 depicts motion sequence of the automatic cell injection system. '(a)-(d)' indicate different cell injection phases, and '*' denotes that loop is executed all the time.

Operation of the system of the present invention may conveniently be carried out on in accordance with the flow chart shown in FIG. 8.

Figure 3:
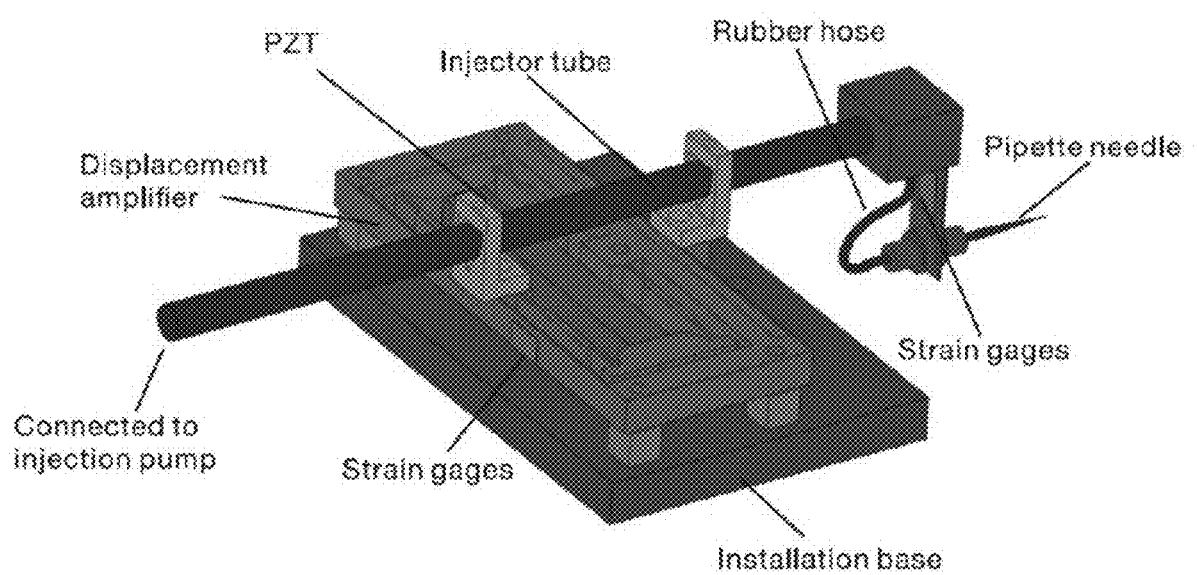
FIG. 3 shows a CAD model of the developed piezo-driven injector with strain-gage position and force sensors. The moropipette is fixed on the injector tube through the force sensor and the injector tube id mounted on the top of the linear actuator by two supports.
Figure 4:
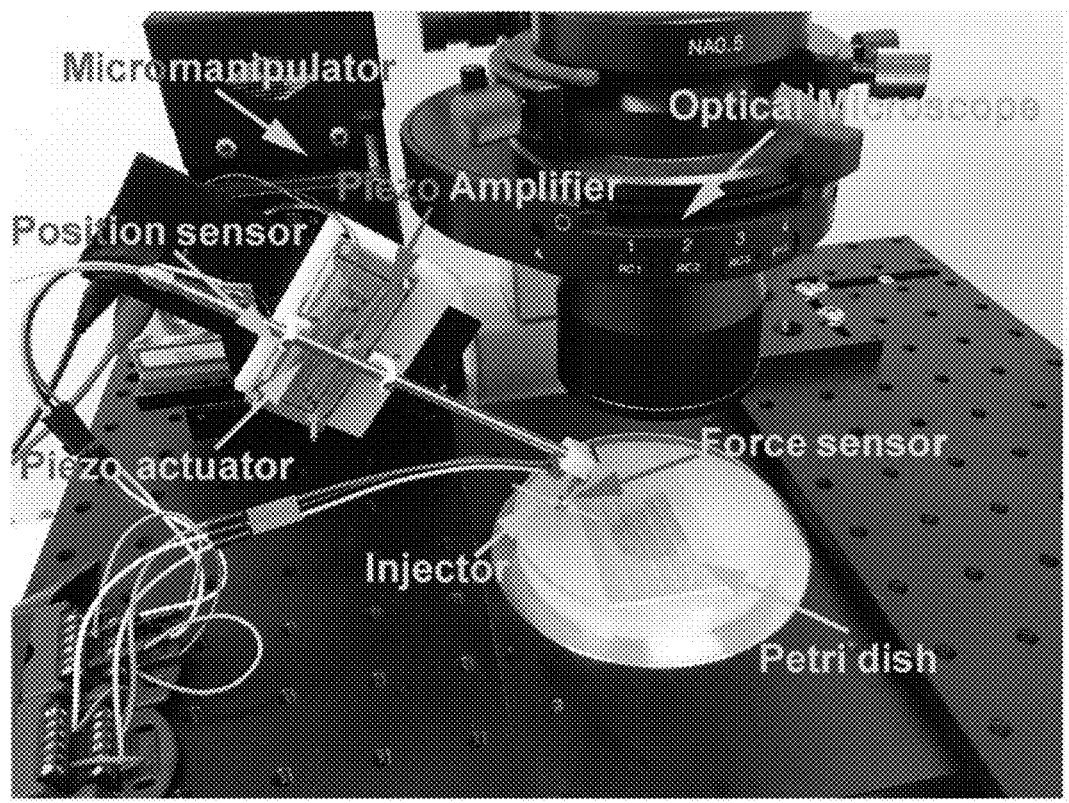
FIG. 4 shows an experimental setup for cell injection.

FIG. 3 illustrates a CAD model of the designed flexure-based injector along with PZT actuator and strain-gage sensors of the present invention. A prototype of the flexure-based injection mechanism is developed as depicted in FIG. 4 later. It is fabricated with Al-7075 alloy using wire electrical discharge machining. The mechanism is driven by a piezoelectric actuator (PEA) (model: P-885.91, from Physik Instrumente, Co.). The PEA is actuated by a high-voltage amplifier (model: EPA-104, from Piezo System, Inc.), by which the voltage will be enlarged by ten times to drive the flexure-based compliant injector and deliver a maximum displacement of 200 µm. Moreover, FEA simulation study shows that an output displacement of 301 µm is achieved when the payload load of the injector is applied in the vertical out-of-plane direction. As compared with FEA simulation result, the experimental result is 33% smaller. The discrepancy is mainly caused by the manufacturing error of the device parameters and estimation error of the preloading.

Two half-bridge circuits are constructed by semiconductor strain gages (model: TP-3.8-350, from Bengbu Tianguang Sensor, Ltd.), which are adopted to measure the output displacement of this stage and applied force on the injection needle. The laser sensor (model: LK-H055, from Keyence Corp.) and load cell (model: GSO-10, from Transducer Technology, Inc.) are used for the calibration of the position and force sensing strain gages, respectively. A thick-walled glass capillary (borosilicate glass B100-50-10 from Sutter Instrument Co.) was pulled using micropipette puller (P-1000, Sutter Instrument Co.) to get an appropriate outer diameter (3 µm) of the injection needle. The inverted microscope (model: IX81, from Olympus, Inc.) has an XY stage for positioning the petri dish. Zebrafish embryos are placed in parallel V-grooves, which are made from the 1.5% agarose gel in a petri dish. The injector can move in plane for the embryos in each groove, which simplifies 3D movement to plane motion in each groove. The calibration and experiments with zebrafish embryos are conducted at the room temperature of 24° C.

The cell injection control algorithm is implemented on Natural Instruments (NI) cRIO-9022 real-time controller integrated with cRIO-9118 reconfigurable chassis, which contains a Field-Programmable Gate Array (FPGA) module. In addition, NI-9263 analog output module with 16-bit resolution and NI-9237 bridge analog input module with 24-bit resolution are employed to produce the excitation voltage and obtain the strain gage sensor signals, respectively. The sampling rate of the system is selected as 4 kHz.

In cell injection, a majority of force sensors are designed with Polyvinylidene Fluoride (PVDF) film [8,11,12,23], which have a remarkable dynamic force detection ability. However, the dynamic sensor is not suitable for the sensing of quasi-static signals. Alternatively, with the advantages of higher unit resistance and sensitivity, semiconductor strain gages are used as force sensors in this work. It works based on the piezoresistive effects of silicon and measures the change in resistance due to the accompanied strain.

Figure 5:
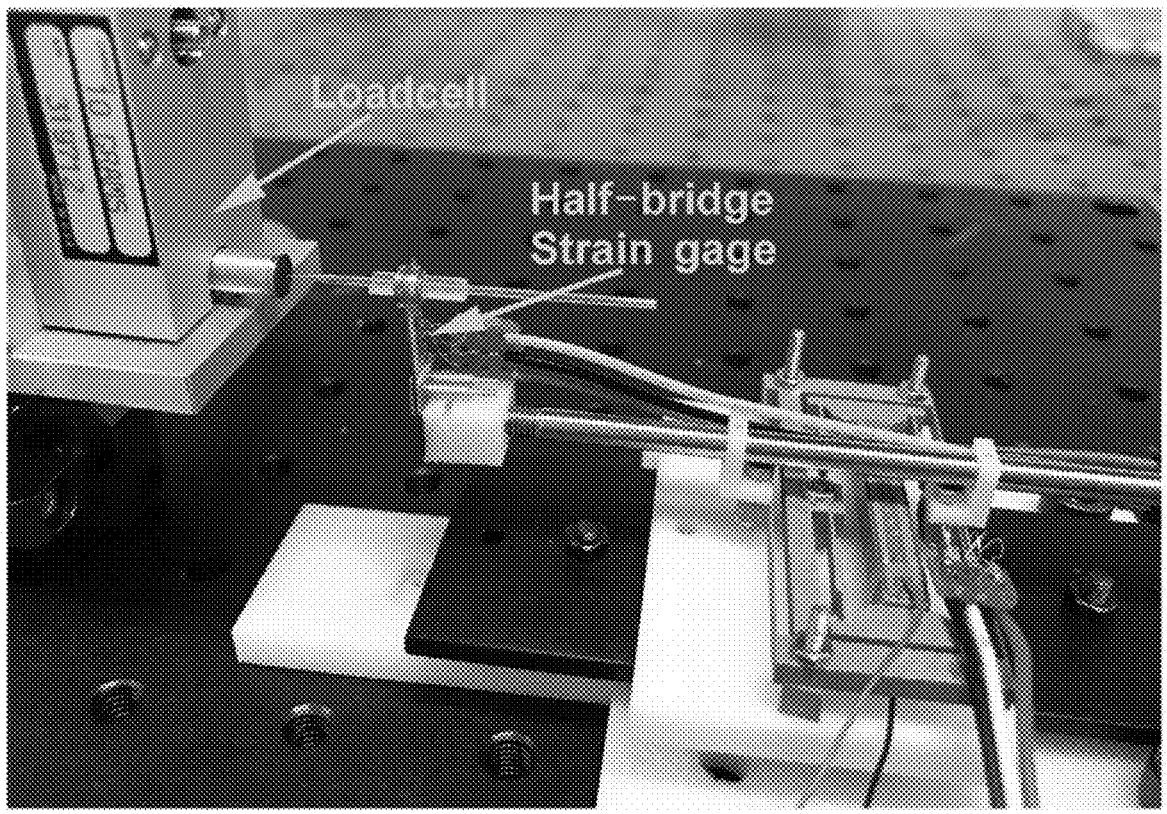
FIG. 5 shows an experimental setup for force sensor calibration.

Two strain gages are mounted on a cantilever-beam mylar (see FIG. 4) to construct a half-bridge circuit. It is adopted to measure the injection force in this work. The experimental setup for the calibration of the developed force sensor is shown in FIG. 5. The commercial loadcell (model: GSO-10, from Transducer Techniques Corp.) with a maximum measurement range of 98.1 mN and resolution of 50 µN is adopted. It is mounted on a 3-DOF high precision positioning stage (model: HTCL25-X, from Huntington Optics, Inc.). An approximate linear relation between the loadcell and strain gage signal values is observed. The sensitivity of strain gages is estimated as −14.204 mN/mV.

Figure 6:
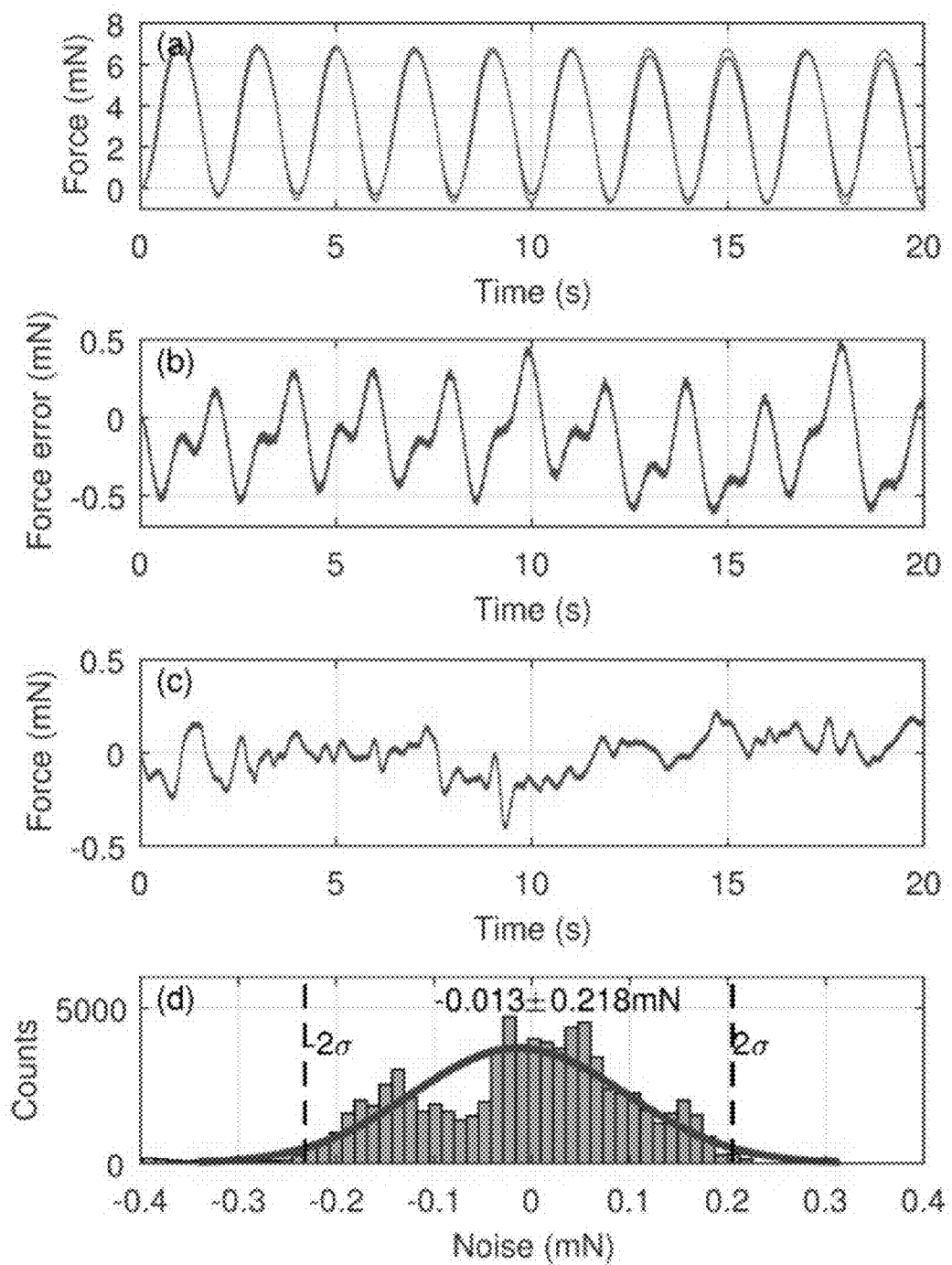
FIG. 6 shows force sensor calibration result (a) The output of loadcell sensor and strain gages; (b) Force calibration error; (c) Strain gage force sensor noise; (d) Histogram of strain gage sensor noise.

FIGS. 6(a) and (b) show that the output of the calibrated strain gage force sensor matches well with the readings of loadcell sensor. However, their greater sensitivity to temperature variations and tendency to drift are disadvantages in comparison to PVDF sensors. The temperature drift is notable, as shown in FIG. 6(c), and its 2 σ resolution [24] can be obtained as 0.218 mN (see FIG. 6(d)).

Figure 7:
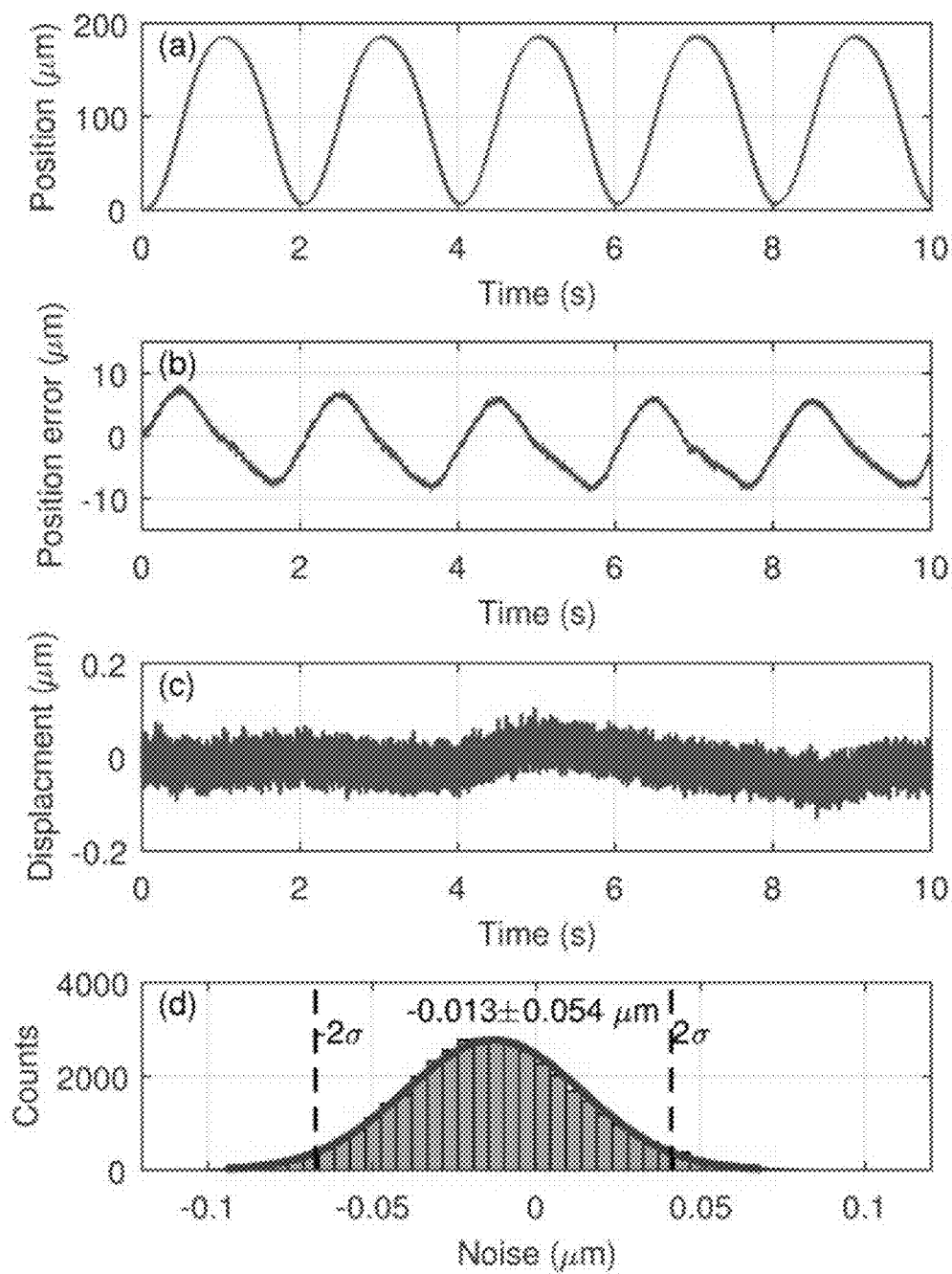
FIG. 7 shows position sensor calibration result. (a) The output of laser sensor and strain gages; (b) Position calibration error; (c) Strain gage position sensor noise; (d) Histogram of strain-gage sensor noise.

To construct a half-bridge circuit for the position measurement, two strain gages are mounted on the flexure of displacement amplifier, as shown in FIG. 4. For the position sensor calibration, the displacement of the pipette is measured by a laser displacement sensor (model: LKH055, from Keyence Corp.), and the corresponding output value of strain-gage sensor is recorded. The linear relation between the laser output and strain gage values is found, and the sensitiveness of strain gages is estimated as −14.42 µm/mV. It can be found from in FIGS. 7(a) and (b) that the calibrated strain-gage sensor matches well with the laser sensor. When a zero voltage input is applied, the noise of the strain-gage sensor is sampled as shown in FIG. 7(c). The noise follows a normal distribution as shown in FIG. 7(d). Therefore, the 2 σ resolution of the strain gage position sensor can be obtained as 0.054 µm.

By inspecting the results in FIGS. 6(c) and 7(c), it is observed that the temperature drift is decreased in the position sensor in comparison with the force sensor using the same half-bridge signal conditioning circuit. The reason may lie in that the temperature on position sensor is more stable than that on force sensor. The displacement amplifier, which is made from aluminum material, has a better thermal conductivity than the flexure material of mylar for the force sensor. As a result, the imperceptible temperature change has less influence on the position strain-gage sensor.

The measurement range and sampling rate of position and force sensors are limited by the equipment used. For example the NI-9237 bridge module, has ±25 mV analog input range and 50 Ks/s sampling rate. Hence, although a force measurement range with ±355 mN and position measurement range with ±360 µm can be achieved in theory, these ranges may be more limited in due to the initial installing deformation.

To compare the performances of cell injection system with the traditional position control and position/force control during cell puncturing process, the same controller structure is adopted. In particular, owing to its popularity and model-free nature, the incremental PID controller is employed as the position and force controllers for cell injection system. By defining $e(t)=x(t)-x_r(t)$ as the position/force tracking error, the control action is derived as follows.

$$u(t)=u(t-T)+K_p[e(t)-e(t-T)]+K_ie(t)+K_d[e(t)-2e(t-T)+e(t-2T)] \quad (3)$$

where x is position/force variable, $x_r$ denotes the desired position/force trajectory, T is the sampling time interval, and u(t−T) denotes the control variable in the previous time step, $K_p$, $K_i$ and $K_d$ are the positive gains to be tuned.

For cell microinjection testing, the fabricated injector is mounted on an XYZ micromanipulator (model: MP-285, from Sutter Instrument Corp) to develop an automatic cell injection system. In the experimental study, a batch of zebrafish embryos are immobilized on the V-groove agarose gel in a petri dish, which is placed on the platform of an inverted microscope. The injector tip can move in plane for embryos in each V-groove. After the initialization and calibration of the CCD camera, the relative position between the pipette and target embryo can be recognized with computer vision algorithm. The micropipette moves from the initial position to the target cell controlled by the XYZ micromanipulator first. Once the pipette needle contacts with the embryo, which can be detected by the integrated force sensor, the coarse movement of micromanipulator is switched to the precision control of the piezo-driven injector. Two control schemes are realized in this work, i.e. (a) the traditional injection sequence with position control and (b) the improved operation flow with force control intervened.

A predefined position/force trajectory is used as a reference based on the trigger value for pipette puncturing until a dramatic force drop is detected. Then, a time interval is reserved to execute practical injection task, i.e. injecting the desired material. After that, a gentle retracting movement is applied under the precise position control to avoid throwing out the injected material by the retracting pipette. Finally, when the piezoelectric actuator returns to its home position, the micromanipulator translates back with a safe distance to prevent the pipette needle from crashing into the embryo during moving to the next embryo. When the next embryo comes into camera view, the above injection process is repeated. The motion sequence is shown in FIG. 8.

Experimental Study and Results

In this section, experimental study on cell injection is carried out using the developed injector with the foregoing control schemes.

Cell Injection Experiments

In practice, majority of unsuccessful cell injections are caused by the fact that, the computer believes that the target cell had been punctured while the pipette needle did not do that in reality. Actually, it is difficult to distinguish with the visual feedback whether the target embryo has contacted with micropipette or just slipped over.

Figure 9:
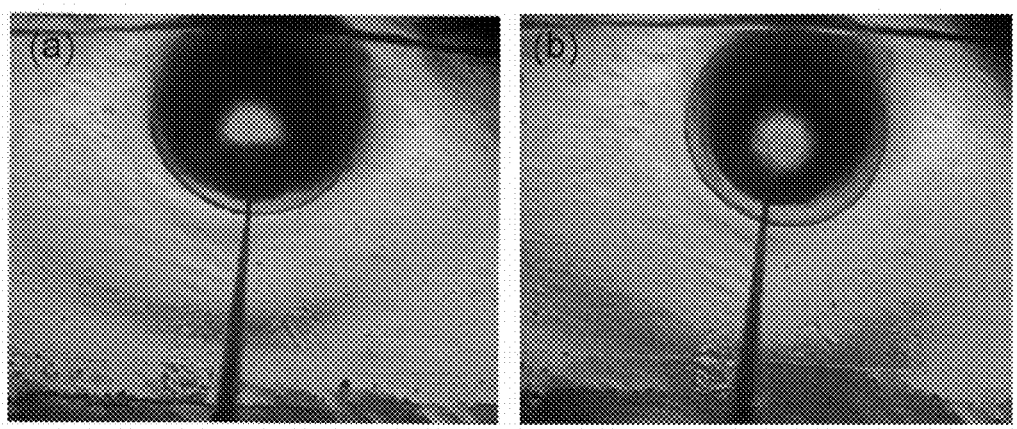
FIG. 9 shows a comparison between different injection scenarios. (a) Micropipette is puncturing the embryo; (b) micropipette slips over the embryo.
Figure 10:
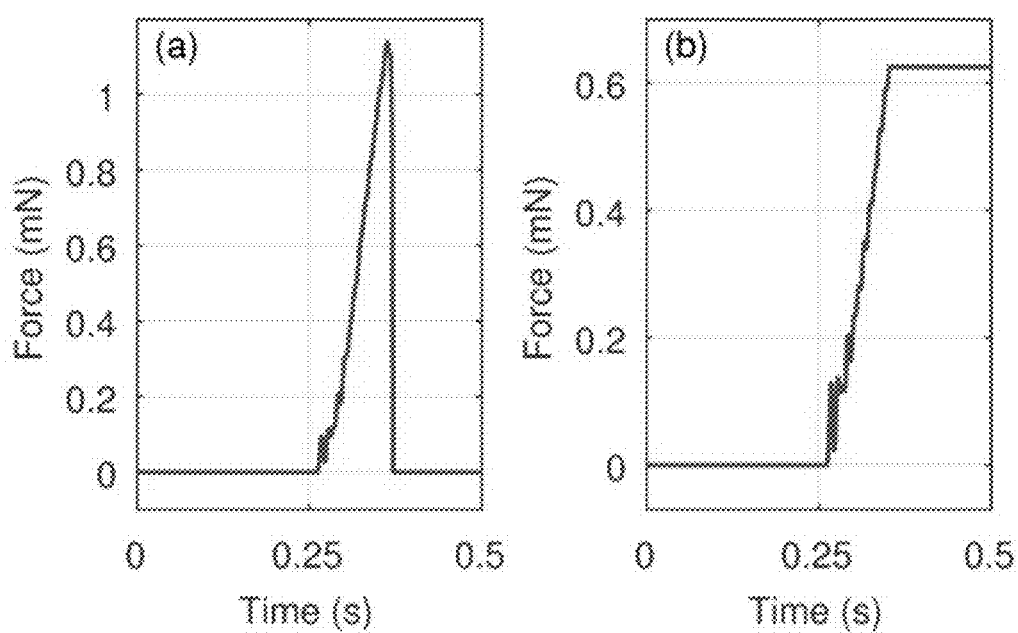
FIG. 10 depicts force sensor output signals during the cell injection. (a) Force variation of pierced cell; (b) force variation of unpierced cell.

For example, two injection scenarios are depicted in FIG. 9. FIG. 9(a) shows that the pipette is puncturing the embryos while FIG. 9(b) illustrates the case when the pipette slips over. There is no clear difference between these two scenarios in the pictures. Adding another camera to monitor the vertical movement of pipette can be a possible solution [25]. But it increases the system complexity at the same time. Alternatively, with the force feedback, the problem is easier to solve. Specifically, when the pipette needle contacts with target embryo, the force sensor will give a force feedback. Moreover, it is easy to identify the cell injection state, i.e. whether pierced or unpierced. The force feedback will drop dramatically once the cell membrane is punctured, which can be detected by the integrated force sensor in the proposed injection system. For instance, FIG. 10 shows the force sensor output signals for the pierced and unpierced cells. The difference between the pierced and unpierced situations can be identified easily from the force curves.

Figure 11:
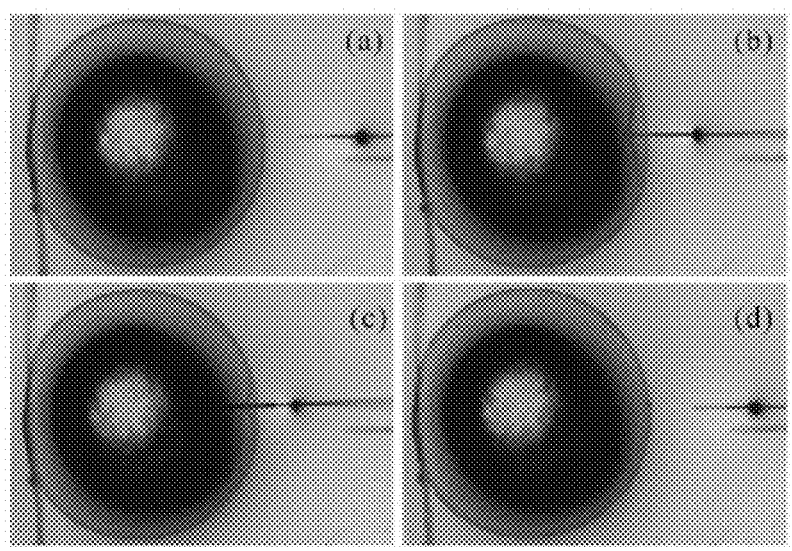
FIG. 11 shows injection phases of the zebrafish embryo. (a) Approaching phase; (b) penetration phase; (c) injecting phase; (d) retracting phase.

The collected embryos are spread on the V-grooves and aligned with manual assist carefully. A total of 100 zebrafish embryos are divided into to two equal groups, which are continuously injected using the proposed injection system with position and force control, respectively. The average injection time for each embryo is reduced to less than 3 s, which is better than that of a proficient human operator. The injection speed is set as 2 mm/s and 20 mN/s for position and force control, respectively. A gentle retracting speed is set as 220 μm/s. The force trigger threshold from coarse to fine movement is 500 μN, the punctured force velocity trigger is −10 mN/s. In addition, once the embryo is pierced, a period of 500 ms is reserved to inject the desired material. The safe distance of coarse movement is set as 5 mm. By trial and error, the parameters of PID position controller are tuned as $K_p=2\times10^{-3}$, $K_i=6\times10^{-4}$, and $K_d=1.5\times10^{-3}$. The parameters of PID force controller are adjusted as $K_p=6\times10^{-3}$, $K_i=9\times10^{-4}$, and $K_d=1\times10^{-3}$. FIG. 11 shows the sequence pictures during the microinjection process of a zebrafish embryo. The injected embryos are cultured at room temperature of 24° C.

It is found that the change rate of the temperature drift is quite low (≤10 mN/s). In practice, an efficient and quick manipulation behavior (~20 mN/s) during the cell injection is preferred. Hence, the velocity of variation between the noise and working force can be differentiated conveniently. In this work, a change rate limit of 10 mN/s is used to extract the force signal from noise during algorithm implementation, which means that only a rapid change signal (i.e. puncturing force) can pass this gate while the noise is resisted.

To reduce the temperature drift of strain-gage force sensor further, the motion sequence of the automatic cell injection system is specifically designed. The force output is set as zero before the signal value reaches contact force threshold. The puncturing time is quite short (~0.1 s), which reduces the drift impact further. The force is reset to zero again after each cell membrane is punctured.

Results

Figure 12:
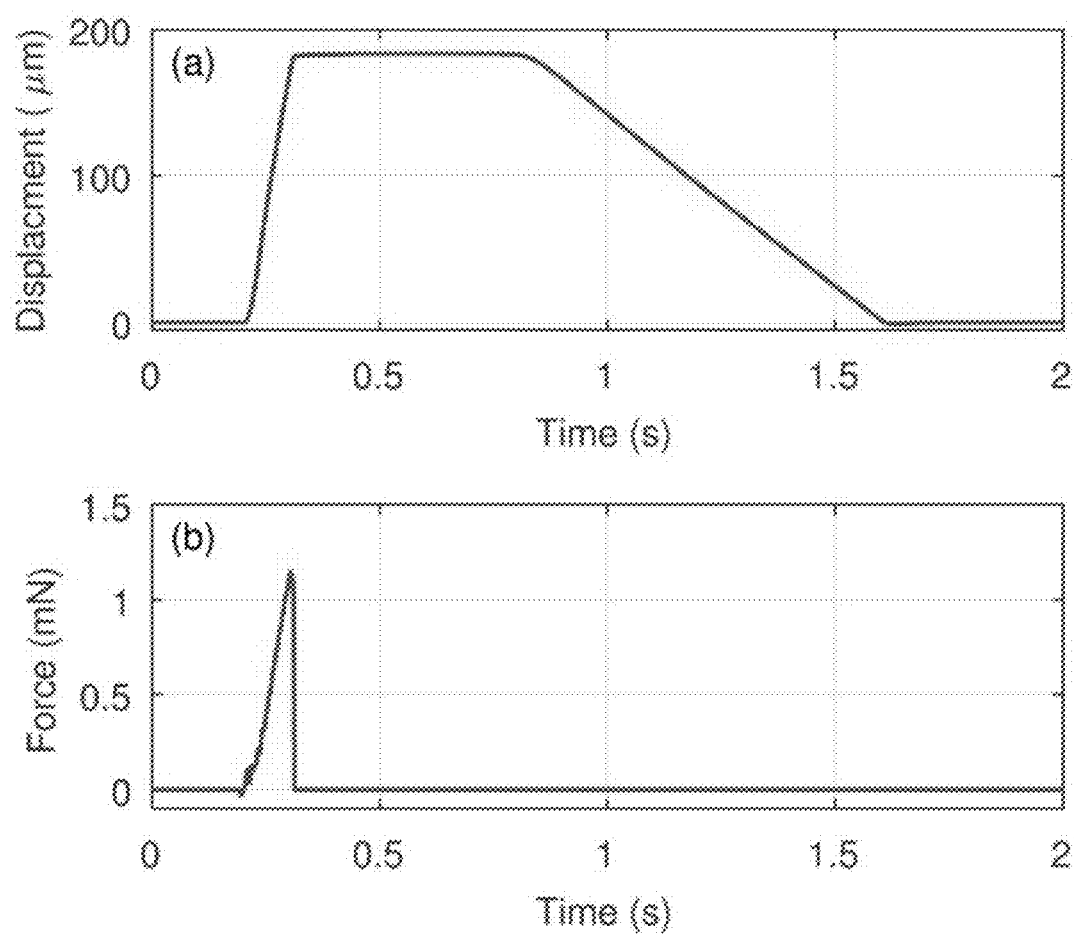
FIG. 12 shows injection results of one zebrafish embryo with position control. (a) position trajectory; (b) force trajectory.
Figure 13:
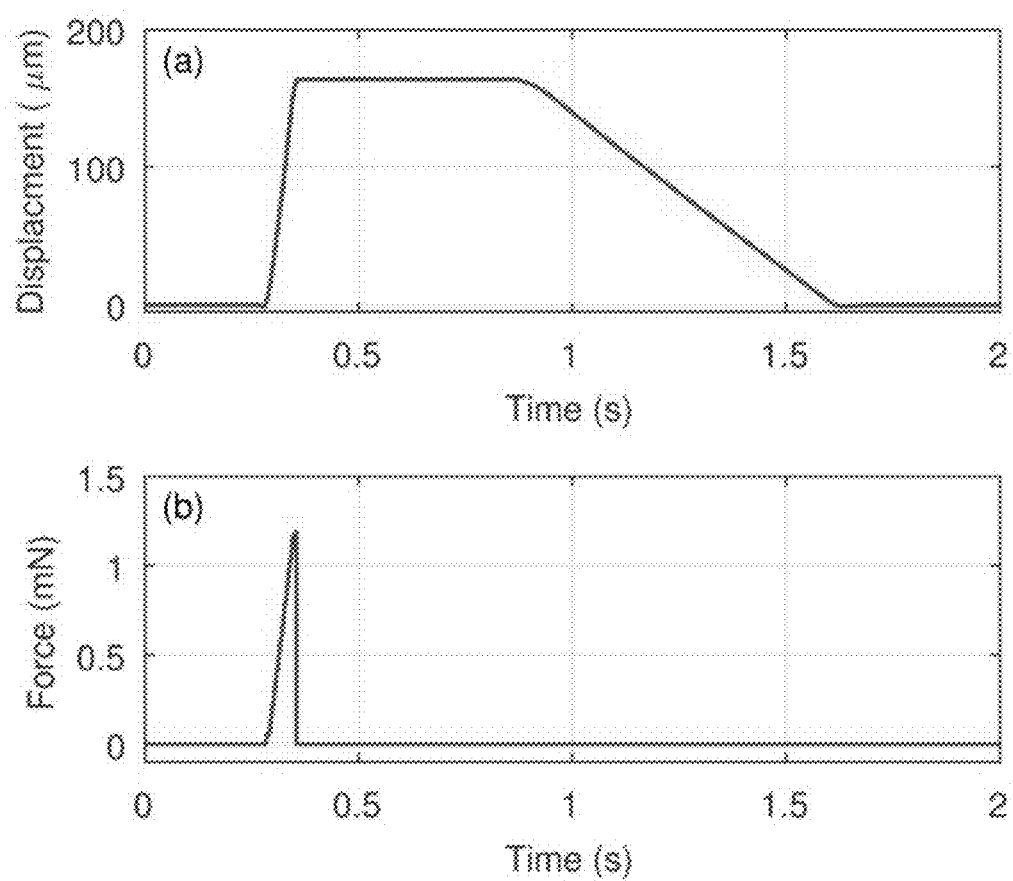
FIG. 13 shows injection results of one zebrafish embryo with force control. (a) position trajectory; (b) force trajectory.

The experimental results of position and force control are shown in FIGS. 12 and 13, respectively. The force trajectory is smoother with force control (see FIG. 13(b)) while there are some burrs in the force trajectory when position control only is used for cell injection (see FIG. 12(b)). In order to quantitatively evaluate the performance of the automated injection system, the success rate and survival rate are usually adopted as evaluation criteria to characterize a cell injection system [26]. The success rate is defined as the ratio between the number of embryos with a dramatic drop force curve and the total number of injected embryos. With the force feedback, the unsuccessfully injected embryos can be detected and eliminated during the cell injection process. In this work, all of the manipulated cells are injected successfully.

The survival rate is defined as the ratio between the number of injected embryos that are capable of developing into larva and the total number of embryos injected. It essentially represents the severity and frequency of cell damage due to the injection. Based on the 100 injected zebrafish embryos with position control and force control, the survival rates are calculated as 82 and 86%, respectively.

TABLE 2

Comparison of experimental results.

| Method | Cell type (number) | Survival rate (%) |
| --- | --- | --- |
| Manual operation | Zebrafish embryo | 50-70 |
| Piezo-drill system [14] | Mouse oocytes (322) | 80 |
| Piezo-driven system [27] | Intracytoplasmic Sperm (25) | 88 |
| Piezo-driven ultrasonic method [19] | Zebrafish embryo (200) | 80.7 |
| Piezo-driven with position control (this work) | Zebrafish embryo (50) | 82 |
| Piezo-driven with force control (this work) | Zebrafish embryo (50) | 86 |

The survival rates obtained by the existing approaches are compared as shown in Table 2. It is observed that the force control produces a higher survival rate than conventional position control in the same operation environment. With force control involved, the achieved survival rate of 86% is better than majority of existing works. It is notable that the survival rate can be further improved with more delicate care during the embryo culturing and precision control algorithm design. Even so, it is better than the survival rate of 50-70% in manual operation which is caused by the proficiency difference and fatigue problems. The improvement of survival rate with force control is dominantly contributed by the smoother force interaction and the greatly reduced embryo deformation.

With the force-controlled injection system, another remarkable improvement is the injection speed. With the advantages of force feedback and PZTs, quick response and assured pierced state are achieved without time delay and misjudgment. Injection time of 3 s per embryo can be achieved, i.e. 20 embryos/min. The injection speed is much quicker than the manual injection speed of about 8-15 embryos/min. In common practical experiments, the cell number to be processed generally is about 300-500. The improvement of the cell manipulation speed can reduce the individual difference effectively for practical applications, such as drug development and gene therapy.

Further improvement of the proposed injection system will be focused on higher-throughput automatic cell injection and force sensor resolution.

Experimental results confirm the superiority of the force control vs. conventional position control in the cell injection system. Despite the difference size between the commonly used objects in biological injection experiments, this proposed system can be easily applied to other cell injection applications, such as mouse oocytes, graine, and other types of suspended cells.

To demonstrate the superiority of the developed system over skilled human operator, practical experimental studies have been conducted. Different from the previous experimental study which mimics the material delivery process, the sgRNA and Cas9 mixture is injected into Zebrafish embryos for gene editing. In this work, the drug dose of 2.2 nL is injected to every cell. Zebrafish embryos are placed in parallel V-grooves in a petri dish, and the V-grooves are made from the 1.5% agarose gel. The petri dish is mounted on an XY stage, which is used along with the microscope. The tip diameter of the adopted injector is around 1 μm and the depth of injection is set as 700 μm.

In each experimental setup, a batch of 69 cells are injected by the automated microinjection system. For more convincing comparison, the same operation is also conducted by a skilled human operator who has more than three years' manual injection experience. The experiment has been repeated by 5 times. Results indicate that the developed microinjection system provides the average injection speed of 3.55 s per cell, which is 42% slower than the skilled manual speed of 2.50 s per cell. On the other hand, the results reveal that the automated system achieves the average cell viability of 46.0%, which is 18% higher than the manual operation result of 39.0%. Moreover, concerning the cell viability, the standard deviation of the microinjection system's result is 0.37, which has been reduced by 91% in comparison with the manual operation result of 4.24.

Considering that the injection speed of the automated system can be greatly enhanced by employing multiple machines working in parallel, the developed microinjection system is superior to manual manipulation in terms of consistency and viability of the injected cells, which are the key indicators of the cell injection quality. Therefore, the experimental results confirm the effectiveness of the developed force-sensing microinjection system for multi-cell injection task. It is notable that the injection speed of the system can be improved by employing more advanced image acquisition and processing hardware.

REFERENCES

[1] Howe K, Clark M D, Torroja C F, et al. The zebrafish reference genome sequence and its relationship to the human genome. Nature. 2013; 496(7446):498-503.

[2] Sun Y, Nelson B J. Biological cell injection using an autonomous microrobotic system. Int J Rob Res. 2002; 21(10-10:861-868.

[3] Yan X, Sun D. Multilevel-based topology design and cell patterning with robotically controlled optical tweezers. IEEE Trans Control Syst Technology. 2015; 23(1):176-185.

[4] Permana S, Grant E, Walker G M, et al. A review of automated microinjection systems for single cells in the embryogenesis stage. IEEE/ASME Trans Mechatron. 2016; 21(5):2391-2404.

[5] Karimirad F, Chauhan S, Shirinzadeh B. Vision-based force measurement using neural networks for biological cell microinjection. J Biomech. 2014; 47(5):1157-1163.

[6] Zhang Y, Tan K K, Huang S. Vision-servo system for automated cell injection. IEEE Trans Indus Electron. 2009; 56(1):231-238.

[7] Ammi M, Ferreira A. Biological cell injection visual and haptic interface. Adv Rob. 2006; 20(3):283-304.

[8] Pillarisetti A, Pekarev M, Brooks A D, et al. Evaluating the effect of force feedback in cell injection. IEEE Trans Autom Sci Eng. 2007; 4(3):322-331.

[9] Shen Y, Fukuda T. State of the art: micro-nanorobotic manipulation in single cell analysis. Rob Biomimetics. 2014; 1(1):1-13.

[10] Lu Z, Chen P C, Nam J, et al. A micromanipulation system with dynamic force-feedback for automatic batch microinjection. J Micromech Microeng. 2007; 17(2):314-321.

[11] Xie Y, Sun D, Tse H Y G, et al. Force sensing and manipulation strategy in robot-assisted microinjection on zebrafish embryos. IEEE/ASME Trans Mechatron. 2011; 16(6):1002-1010.

[12] Huang H B, Sun D, Mills J K, et al. Robotic cell injection system with position and force control: Toward automatic batch biomanipulation. IEEE Trans Rob. 2009; 25(3):727-737.

[13] Xu Q. Digital integral terminal sliding mode predictive control of piezoelectric-driven motion system. IEEE Trans Indus Electron. 2016; 63(6):3976-3984.

[14] Ron-El R, Liu J, Nagy Z, et al. Intracytoplasmic sperm injection in the mouse. Human Reprod. 1995; 10(10: 2831-2834.

[15] Huang T, Kimura Y, Yanagimachi R. The use of piezo micromanipulation for intracytoplasmic sperm injection of human oocytes. J Assisted Reprod Genet. 1996; 13(4): 320-328.

[16] Ediz K, Olgac N. Effect of mercury column on the microdynamics of the piezo-driven pipettes. J Biomech Eng. 2005; 127(3):531-535.

[17] Fan M, Feng Z, Agca Y, et al. Vibration study of the piezodriven pipettes immersed in viscous liquids. J Appl Phys. 2006; 100(7):074701.

[18] Gan Y, Chen Z. A study of the zona piercing process in piezodriven intracytoplasmic sperm injection. J Appl Phys. 2008; 104(4):044702.

[19] Huang H, Mills J K, Lu C, et al. A universal piezodriven ultrasonic cell microinjection system. Biomed Microdevices. 2011; 13(4):743-752.

[20] Avci E, Hattori T, Kamiyama K, et al. Piezo-actuated parallel mechanism for biological cell release at high speed. Biomed Microdevices. 2015; 17(5):1-10.

[21] Xu Q. Precision motion control of piezoelectric nanopositioning stage with chattering-free adaptive sliding mode control. IEEE Trans Autom Sci Eng. 2017; 14(1): 238-248.

[22] Xu Q, Li Y. Analytical modeling, optimization and testing of a compound bridge-type compliant displacement amplifier. Mech Mach Theory. 2011; 46(2):183-200.

[23] Wei Y, Xu Q. Design of a PVDF-MFC force sensor for robot-assisted single cell injection. IEEE Sens J. 2017; 17(13):3975-3982.

[24] Xu Q. Design and smooth position/force switching control of a miniature gripper for automated microhandling. IEEE Trans Indus Inf. 2014; 10(2):1023-1032.

[25] Wang W, Liu X, Sun Y. Contact detection in microrobotic manipulation. Int J Rob Res. 2007; 26(8):821-828.

[26] Wang W H, Liu X Y, Sun Y, et al. High-throughput automated injection of individual biological cells. IEEE Trans Autom Sci Eng. 2009; 6(2):209-219.

[27] Yi Z, KokKiong T, Sunan H. Software based vision system for automated cell injection. Proceedings of International Conference on BioMedical Engineering and Informatics (BMEI 2008); Sanya, China; 2008. p. 718-722.

The invention claimed is:

1. A microinjection system comprising:
a microinjector; and
a control device comprising:
a linear actuator which controls the movement of the microinjector towards and from a pierceable microstructure target; and
position and force strain gauge sensors configured to provide position and force information including force feedback information for enabling making a determination of whether the pierceable microstructure target has been pierced,
wherein the force feedback information is provided to a controller which is operatively linked to said linear actuator,
wherein the control device further comprises a bridge displacement amplifier,
wherein at least one of the force strain gauge sensors is mounted on the bridge displacement amplifier, and
wherein at least another one of the force strain gauge sensors is mounted on the microinjector.

2. The microinjection system as claimed in claim 1, wherein said controller comprises a proportional-integral-derivative controller.

3. The microinjection system as claimed in claim 1, wherein said linear actuator is a piezoelectric actuator with the bridge displacement amplifier.

4. The microinjection system as claimed in claim 1, wherein said force strain gauge sensors are semiconductor strain gauge sensors.

5. The microinjection system as claimed in claim 4, wherein one of the force-strain gauge sensors is configured to control the force applied by the linear actuator to be sufficient to effect puncture of a target.

6. The microinjection system as claimed in claim 1, wherein the microinjector is a micropipette and the microinjection system further comprises a flexure guiding mechanism for driving the micropipette to its intended location and for ensuring withdrawal of the micropipette with minimal damage to the pierceable microstructure target.

7. The microinjection system as claimed in claim 6, wherein the controller is configured to exercise control over movement of the micropipette using sampling time intervals according to equation (3):

$$u(t)=u(t-T)+K_p[e(t)-e(t-T)]+K_i e(t)+K_d[e(t)-2e(t-T)+e(t-2T)] \quad (3)$$

where x is a position/force variable, $x_r$ denotes a desired position/force trajectory, T is the sampling time interval, e(t) is the position/force tracking error, u(t) denotes a control variable of the current time step, and u(t−T) denotes the control variable in the previous time step, and $K_p$, $K_1$ and $K_d$ are tunable positive gains and e(t)=x(t)−$x_r$(t).

8. A method for microinjection of a substance into a pierceable microstructure target which comprises:
(1) positioning a microinjector relative to the pierceable microstructure target by use of a charge coupled device camera using a computer vision algorithm;
(2) following the positioning of the microinjector relative to the pierceable microstructure target, effecting puncture of said pierceable microstructure by the microinjector; and
(3) introducing a substance into said pierceable microstructure by injection from said microinjector,
wherein motion of said microinjector is controlled by a control device comprising a linear actuator which controls movement of the microinjector towards and from said pierceable microstructure target and position and force strain gauge sensors configured to provide position and force information including force feedback information enabling making a determination of whether the pierceable microstructure target has been pierced to a controller which is operatively linked to said linear actuator whereby sufficient force is applied to the microinjector to effect piercing of the wall of the pierceable microstructure,
wherein the control device further comprises a bridge displacement amplifier,
wherein at least one of the force strain gauge sensors is mounted on the bridge displacement amplifier, and wherein at least another one of the force strain gauge sensors is mounted on the microinjector.

9. The method as claimed in claim 8, wherein control over the movement of the microinjector is effected by the controller according to the equation (3):

$$u(t)=u(t-T)+K_p[e(t)-e(t-T)]+K_i e(t)+K_d[e(t)-2e(t-T)+e(t-2T)] \quad (3)$$

where x is a position/force variable, $x_r$ denotes a desired position/force trajectory, T is the sampling time interval, e(t) is the position/force tracking error, u(t) denotes a control variable in the current time step, and u(t−T) denotes a control variable in the previous time step, $K_p$, $K_1$ and $K_d$ are tunable positive gains and $e(t)=x(t)-x_r(t)$.

10. The method as claimed in claim 9, wherein the force strain gauge sensors are calibrated to provide position and force information to the controller to determine said position/force variable.

11. The method as claimed in claim 8, wherein said pierceable microstructure target is selected from the group consisting of such as a biological cells, nuclear envelopes and viral capsids and envelopes using such a piezoelectric actuator.

12. The method as claimed in claim 11, further comprising which comprises introduction of DNA into a cell nucleus.

13. The method as claimed in claim 12, wherein said introduction is effected as part of a gene therapy regimen.

14. The method as claimed in claim 8, wherein DNA is introduced into a virus.

15. The method as claimed in claim 8, wherein said pierceable microstructure target is an ovum or embryo.

16. The method as claimed in claim 15, wherein said introduction is effected to effect in vitro fertilization of an ovum, cloning or insertion of cells, such as stem cells, into an embryo.

17. A control device suitable for use with an injector for injecting biological material into a pierceable microstructure, said control device comprising:

a linear actuator which controls the movement of the injector towards and from a pierceable microstructure target;

position and force strain gauge sensors configured to provide position and force information including force feedback information enabling making a determination of whether the pierceable microstructure target has been pierced to a controller which is operatively linked to said linear actuator; and a bridge displacement amplifier, wherein at least one of the force strain gauge sensors is mounted on the bridge displacement amplifier, and wherein at least another one of the force strain gauge sensors is configured to be mounted on the injector.

* * * * *

UNITED STATES PATENT AND TRADEMARK OFFICE
CERTIFICATE OF CORRECTION

PATENT NO. : 11,732,275 B2  
APPLICATION NO. : 16/364458  
DATED : August 22, 2023  
INVENTOR(S) : Qingsong Xu Page 1 of 1

It is certified that error appears in the above-identified patent and that said Letters Patent is hereby corrected as shown below:

In the Claims

Claim 7, Column 12, Line 39, please delete the phrase "$K_p$, $K_1$ and $K_d$" and replace with "$K_p$, $K_i$ and $K_d$"

Claim 9, Column 13, Line 13, please delete the phrase "$K_p$, $K_1$ and $K_d$" and replace with "$K_p$, $K_i$ and $K_d$"

Signed and Sealed this  
Third Day of October, 2023

*Katherine Kelly Vidal*

Katherine Kelly Vidal  
*Director of the United States Patent and Trademark Office*